United States Patent [19]

McDonough et al.

[11] Patent Number: 5,430,189
[45] Date of Patent: Jul. 4, 1995

[54] PROCESS FOR PREPARING SUBSTITUTED AND UNSUBSTITUTED ARYLALKYLAMINES

[75] Inventors: Joseph A. McDonough; Ahmed M. Tafesh; Olan S. Fruchey, all of Corpus Christi, Tex.

[73] Assignee: Hoechst Celanese Corporation, Somerville, N.J.

[21] Appl. No.: 185,098

[22] Filed: Jan. 19, 1994

Related U.S. Application Data

[62] Division of Ser. No. 957,335, Oct. 6, 1992, Pat. No. 5,319,142.

[51] Int. Cl.$^6$ ............................................. C07C 209/38
[52] U.S. Cl. ................................. 564/423; 564/414; 564/415; 564/420; 564/422
[58] Field of Search ............... 564/423, 420, 422, 415, 564/414

[56] References Cited

U.S. PATENT DOCUMENTS

| | | | |
|---|---|---|---|
| 4,491,628 | 1/1985 | Itoh et al. | 564/337 |
| 5,082,965 | 1/1992 | Nader et al. | 558/270 |
| 5,124,489 | 6/1992 | Durrwachter et al. | 568/630 |

*Primary Examiner*—Allen J. Robinson
*Assistant Examiner*—Brian M. Burn
*Attorney, Agent, or Firm*—James J. Mullen; Donald R. Cassady

[57] ABSTRACT

An arylisonitrosoalkanone is hydrogenated in the presence of a noble metal catalyst and a weak carboxylic acid to form an arylalkanolamine which is then hydrogenated in the presence of a strong mineral acid and the transition metal catalyst to form an arylalkylamine. When the arylisonitrosoalkanone is an isonitrosoacetophenone, the isonitrosoacetophenone is prepared by one of two methods.

In the first method, a substituted or an unsubstituted isonitrosoacetophenone is prepared from a corresponding substituted or unsubstituted acetophenone by oxidizing the acetophenone to form a substituted or an unsubstituted phenylglyoxalacetal in a reactor, hydrolyzing the phenylglyoxal acetal in the same reactor to form a corresponding substituted or unsubstituted phenylglyoxal, and condensing the phenylglyoxal with hydroxylamine or a salt thereof in the same reactor to form the substituted or unsubstituted isonitrosoacetophenone. Alternatively, the substituted or unsubstituted isonitrosoacetophenone is prepared from the corresponding substituted or unsubstituted acetophenone by reacting the substituted or unsubstituted acetophenone in water with a source of a nitrosonium ion in the presence of a strong acid to form a corresponding substituted or unsubstituted phenylglyoxal, and condensing the phenylglyoxal with hydroxylamine or a salt thereof to form the substituted or unsubstituted isonitrosoacetophenone. In either method, any strong acid that might be present in the reaction mass following the condensation to the isonitrosoacetophenone shall be removed therefrom prior to initiating the hydrogenation of the isonitrosoacetophenone to the arylalkanolamine.

6 Claims, No Drawings

PROCESS FOR PREPARING SUBSTITUTED AND UNSUBSTITUTED ARYLALKYLAMINES

This application is a divisional of patent application Ser. No. 07/957,335 filed Oct. 6, 1992, now U.S. Pat. No. 5,319,142.

This application is related to U.S. patent application Ser. No. 07/628,238, filed on Dec. 13, 1990 now U.S. Pat. No. 5,120,855 and entitled "Process for the Preparation of Arylalkylamines & Substituted Arylalkylamines"; U.S. patent application Ser. No. 07/850,626, filed on Mar. 13, 1992, now abandoned, and entitled "Process for Preparing Substituted & Unsubstituted Phenylglyoxals from Corresponding Substituted & Unsubstituted Acetophenones"; U.S. patent application Ser. No. 07/698,504, filed on May 10, 1991, now U.S. Pat. No. 5,220,065, entitled "Method for the Preparation of Arylalkanolamines"; and U.S. patent application Docket No. N-7331 filed concurrently herewith, now U.S. Pat. No. 5,319,142, and entitled "Process for Preparing Substituted & Unsubstituted Isonitrosoacetophenones from Corresponding Substituted & Unsubstituted Acetophenones."

TECHNICAL FIELD OF THE INVENTION

The present invention relates to unsubstituted and substituted arylalkylamines and, more particularly, to methods for the preparation thereof. Still more particularly, the present invention discloses methods for preparing unsubstituted and substituted arylalkylamines from corresponding unsubstituted and substituted arylisonitrosoalkanones and from corresponding unsubstituted and substituted acetophenones.

BACKGROUND OF THE INVENTION

Unless stated otherwise, as used herein, the terms "arylalkylamine", "arylalkanolamine", "arylisonitrosoalkanone" and "acetophenone" shall mean an unsubstituted or substituted arylalkylamine, arylalkanolamine, arylisonitrosoalkanone and acetophenone, respectively.

Arylalkylamines are well known compounds which are useful and important chemical intermediates. They are used in the preparation of pharmacologically active compounds and, in some instances, are themselves pharmacologically active. For example, phenethylamine and hydroxyphenethylamine (tyramine) have sympathomimetic (adrenergic) action. Tyramine also is a moiety in opiates, and is useful as an intermediate or substituent in the preparation of other physiologically active compounds or compositions. Hydroxyltyramine (dopamine) is a physiologically important neural inhibitory transmitter.

U.S. Pat. No. 5,041,609 discloses a method of preparing arylalkylamines. An arylalkylketone is reacted with a lower alkyl nitrite in the presence of hydrogen chloride in a dipolar aprotic solvent to produce a reaction mixture which includes an aryl-α-oximinoalkyl ketone. Water is added to the mixture and the aryl-α-oximinoalkyl ketone is extracted from the aqueous reaction mixture with an organic solvent to produce a water free solution of the aryl-α-oximinoalkyl ketone. The water free solution is combined with a supported metal hydrogenation catalyst, a carboxylic acid and a strong inorganic acid. Then, hydrogen is added to produce a salt of the strong acid and an arylalkylamine derived from the aryl-α-oximinoalkyl amine.

U.S. Pat. application Ser. No. 07/630,127, now abandoned, discloses a method for the preparation of the ammonium salt of an arylalkylamine. An aryl-α-oximinoalkyl ketone is reacted with hydrogen in an aqueous reaction medium comprising hydrochloric acid and a noble metal catalyst to produce a reaction product comprising the salt of an arylalkylamine as its major component.

U.S. Pat. application Ser. No. 07/698,504 discloses a method of preparing an arylalkanolamine by hydrogenating an arylisonitrosoalkanone in the presence of a supported noble metal catalyst in a reaction medium comprising a weak carboxylic acid. The arylalkanolamine is obtained in the amine acylate salt form thereof which can then be converted to the hydrochloride salt thereof by reacting the same with hydrogen chloride in a reaction medium comprising an alkyl alcohol.

Tyramine is described in the literature as produced by the sodium in ethanol reduction of p-hydroxyphenylmethylcyanate, *J. Chem. Soc.* v. 9:5, p. 1127 (1909); by the platinum catalyzed hydrogenation of p-hydroxyphenylmethylcyanate, Buck, J.S., *J. Am. Chem. Soc.* v. 55, p. 3389 (1933); and by a lactobacillus decarboxylation of 1-(p-hydroxyphenyl)-2-aminopropionic acid, Umezi, M. et al., *Hakko Kogaku Kaishi* v. 55(2), pp. 68–74 (1977). Other roots for obtaining phenylethylamines via reduction of either vinyl nitro groups, N-N-dibenzylamino groups, or alkylcyanides are known. The reagents used are hydrazine, $NaBH_4$ and hydrogen over platinum.

One disadvantage of some or all of the above processes is that the starting materials are waste intensive, unsafe, and expensive. Another disadvantage is the conversion rates are not very high. Still another disadvantage is that they require the use of large amounts of catalysts.

U.S. Pat. Nos. 1,995,709 ("U.S. Pat. No. '709") and 2,517,906 ("U.S. Pat. No. '906") disclose -a multi-operations procedure for the preparation of substituted phenyl propanol amines, and, more particularly, the preparation of 1-(p- or m-hydroxyphenyl)-2-amino-1-propanol (in U.S. Pat. No. '709), and 1-(p-aminophenyl)-2-amino-1-propanol (in U.S. Pat. No. '906). In U.S. Pat. No. '709, p- or m-hydroxypropiophenone is reacted with a lower alkyl nitrite in ether in the presence of hydrogen chloride to produce p- or m-hydroxyisonitrosopropiophenone, which then is separated from the reaction mixture by alkaline extraction and recovered from the alkaline solution by precipitation induced by acidification of the extract, after which the precipitate is recrystallized. The p- or m-hydroxyisonitrosopropiophenone thus separated is then reacted with hydrogen in the presence of palladium on charcoal in absolute alcohol containing dry hydrogen chloride until reduction stops, after which the amino ketone is recovered as a filtrate. The filtrate is dried and purified by recrystallization. Then, the amino ketone is dissolved in water and reacted with hydrogen in the presence of palladium on charcoal. The reaction product is recovered as the hydrochloride of the amino alcohol, for example, the hydrochloride of 1-(p-hydroxyphenyl)-2-aminopropanol (in U.S. Pat. No. No. '709) and the hydrochloride of 1-p-aminophenyl)-2-aminopropanol (in U.S. Pat. No. '906).

U.S. Pat. No. No. 2,505,645 employs the acidic catalytic hydrogenation process described in U.S. Pat. No. '709 and U.S. Pat. No. '906 in a method of preparing α-phenyl-β-hydroxyphenyl-β-hydroxyethylamine.

U.S. Pat. No. No. 2,784,228 describes a partially aqueous process for the catalytic reduction of α-oximino ketones using alkaline solutions instead of acidic solutions to obtain a desired amino alcohol.

U.S. Pat. No. No. 3,028,429 describes a process for the hydrogenation of isonitrosopropiophenone to produce 1-phenyl-2-aminopropanol. The process is a modification claimed to improve the yields of the general process described in U.S. Pat. No. '709 and U.S. Pat. No. '906.

U.S. Pat. No. No. 3,966,813 discloses a process for preparation of 1-p-hydroxyphenyl)-2-aminoethanol, otherwise referred to as octopamine, by reacting a hydroxyacetophenone with a lower alkyl nitrite in a dipolar aprotic solvent in the presence of a hydrogen chloride catalyst to form isonitrosoacetophenone, and, then, catalytically hydrogenating the isonitrosoacetophenone in the presence of palladium to reduce the isonitroso- and keto- moieties on the isonitroso-acetophenone molecule. The dipolar aprotic solvent is relatively expensive. The yields are about 70 to 80 percent. That patent provides several examples for the preparation of both m-hydroxyisonitrosoacetophenone and p-hydroxyisonitrosoacetophenone. Example 4 describes the hydrogenation step for the conversion of a hydroxyisonitrosoacetophenone to a 1-(hydroxy-phenyl)-2-aminoethanol. That example pertains to hydrogenation of the meta-substituted hydroxyisonitrosoacetophenone.

The present invention discloses improved methods for the preparation of arylalkylamines from corresponding arylisonitrosoalkanones and acetophenones. The methods involve fewer steps for the addition of reactants, avoid the use of toxic materials and complicated extraction procedures, and result in higher conversions than the prior methods.

These and other advantages and objects of the present invention will become apparent from the following description.

SUMMARY OF THE INVENTION

An arylalkylamine is prepared by fast, hydrogenating an arylisonitrosoalkanone in the presence of a noble metal catalyst in a reaction medium comprising a weak carboxylic acid to form an arylalkanolamine. Then, a strong mineral acid is added and the arylalkanolamine is hydrogenated in the presence of such acid to form the arylalkylamine product as an arylalkylammonium salt.

In the case where the arylisonitrosoalkanone is an isonitrosoacetophenone, the method is integrated with methods in which an isonitrosoacetophenone is prepared from a corresponding acetophenone. In the fast integrated method, the acetophenone is reacted, in a first step, with a primary or a secondary alkyl alcohol in the presence of a source of a hydrogen ion and a source of a nitrosonium ion to form a corresponding phenylglyoxal acetal. The source of the hydrogen ion is a strong mineral acid such as hydrochloric acid or sulfuric acid. The source of the nitrosonium ion is an alkyl nitrite or a nitrite salt used in combination with an acid source such as sulfuric acid or hydrochloric acid or a compound NO+X− available from an outside source wherein X is a halogen, an acetate, a sulfate, or a phosphate. The phenylglyoxal acetal is then hydrolyzed, in a second step, in the same reactor to form a corresponding phenylglyoxal. Alcohol or alcohols formed during the second step are immediately removed by vaporization. The phenylglyoxal is then condensed, in a third step, with hydroxylamine in the presence of an acid to form the isonitrosoacetophenone. Any strong acid which is present in the reaction medium is then removed therefrom so that the hydrogenation of the isonitrosoacetophenone in the presence of the weak carboxylic acid and the transition metal catalyst can be initiated as described above.

In the second integrated method, an acetophenone is reacted, in a first step, with a source of a nitrosonium ion in water in the presence of a strong acid to form a substituted or an unsubstituted phenylglyoxal directly in a reactor. The source of the nitrosonium ion is a nitrite salt which reacts with the acid to generate the nitrosonium ion in situ or a compound NO+X−, as defined above, which is brought in to the reactor from an external source. The phenylglyoxal is then condensed, in a second step, in the same reactor with hydroxylamine in the presence of an acid to form the isonitrosoacetophenone. Like in the previous embodiment, any strong acid is then removed from the reaction medium in order to carry out the hydrogenation of the isonitrosoacetophenone in the presence of the weak carboxylic acid as previously described.

An advantage of the invention is that the reaction steps through which a substituted or unsubstituted acetophenone is converted to a substituted or an unsubstituted isonitrosoacetophenone may be carried out in a single reactor using solvents which are compatible in each step.

DETAILED DESCRIPTION OF THE INVENTION

I. Process for the Preparation of an Arylalkylamine from an Arylisonitrosoalkanone According to the present invention, an arylisonitrosoalkanone of the formula:

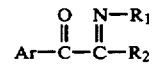

hereinafter "Formula I") is hydrogenated in the presence of a supported noble metal catalyst in a reaction medium comprising a weak carboxylic acid of the

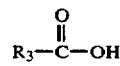

(hereinafter "Formula II") to form an arylalkanolamine of the formula:

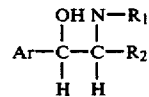

(hereinafter "Formula III"). Then, the arylalkanolamine of Formula III is further hydrogenated in the presence of the same noble metal catalyst by adding a strong mineral acid of the formula HX (hereinafter "Formula IV") to form an arylalkylamine

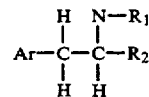

hereinafter "Formula V"). In Formulas I, III and V, Ar represents an unsubstituted phenyl or naphthyl radical, a substituted phenyl radical substituted at one or more of the ortho, para, or meta positions or a substituted naphthyl radical substituted at one or more of the substitutable positions wherein the substituents to the phenyl or naphthyl radicals are independently selected from the groups of hydroxyl radicals, alkoxy radicals, acyloxy radicals, substituted or unsubstituted branched or unbranched alkyl radicals $R_4$ containing one to five carbon atoms, substituted or unsubstituted phenyl radicals $R_5$, and substituted or unsubstituted benzyl radicals $R_6$. The substituted alkyl radicals $R_4$ are substituted in one or more positions with radicals which are independently selected from the group of halogen, hydroxyl, sulfonic acid and sulfuric acid radicals. The substituted phenyl radicals $R_5$ and the substituted benzyl radicals $R_6$ are independently substituted in one or more positions with radicals selected independently from the group of hydroxyl radicals, sulfonic acid radicals, sulfinic acid radicals, alkyl radicals having one to five carbon atoms, and alkoxy radicals having one to five carbon atoms.

In Formula I, $R_1$ represents a hydroxyl, an alkyloxy or a benzyloxy radical. In Formulas I, III and V, $R_2$ represents hydrogen or a $C_1$–$C_8$ alkyl or a cycloalkyl radical. Furthermore in Formula II, $R_3$, represents a $C_1$–$C_{10}$ alkyl, cycloalkyl, aryl or arylalkyl radical. Furthermore, in Formula IV, X represents a chloride, a sulfate, a phosphate, methansulfonate, iodine perchlorate, or bromide radicals. Unless stated otherwise, the above definitions of Ar, $R_1$, $R_2$, $R_3$, and X shall be applicable hereinafter.

An example of an arylisonitrosoalkanone of Formula I is p-hydroxyisonitrosoacetophenone ("HINAP") which is hydrogenated in the presence of a weak carboxylic acid such as acetic acid to form l(hydroxyphenyl)-2-aminoethanol ("Octopamine") which is, then, hydrogenareal in the presence of a strong mineral acid to form p-hydroxyphenethylamine ("Tyramine") as the ammonium salt.

The first step of the present invention, i.e. the hydrogenation of the arylisonitrosoalkanone to the arylalkanolamine, is stoichiometrically represented as follows ("Reaction 1"):

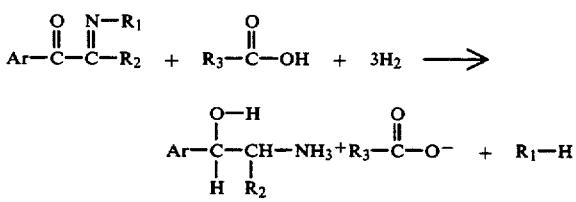

The second step of the present invention, i.e. the hydrogenation of the arylalkanolamine to the arylalkylamine is stoichiometrically represented as follows ("Reaction 2"):

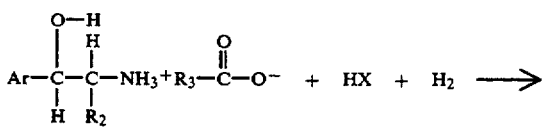

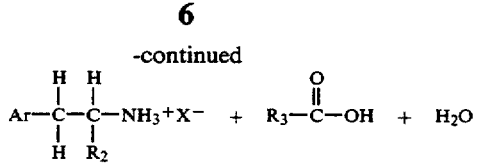

It should be noted that because of the presence of the weak carboxylic acid of Formula II, the arylalkanolamine of Formula III exists as the alkyl ammonium salt of the arylalkanolamine, as shown in the fight hand side of Reaction 1. Similarly, because of the presence of the strong mineral acid of Formula IV, the arylalkylamine of Formula IV exists as the appropriate ammonium salt of the arylalkylamine as shown in the right hand side of Reaction 2.

In carrying out the invention, the arylisonitrosoalkanone reactant, the noble metal catalyst and the weak carboxylic acid acyl donor are charged to a reactor to carry out the first hydrogenation step, i.e. the conversion to arylalkanolamine. It is necessary that this hydrogenation step be carried out in the absence of a strong acid to insure the conversion to the arylalkanolamine. The reactor is placed into positive hydrogen pressure in the range from about 15 to about 500 psig, preferably in the range from about 50 to about 100 psig. The pressure of the hydrogen is maintained within that range during both hydrogenation steps to ensure diffusion of hydrogen to the liquid reaction medium.

Any weak carboxylic acid such as acetic, propanoic, butanoic, pentanoic, hexanoic, heptanoic, octanoic, nonanoic, or decanoic acid may be used in the first hydrogenation step of the invention. The preferred weak acid is acetic acid. The weak carboxylic acid is also used as a solvent, alone, or preferably, together with water. The amount of carboxylic acid used is sufficient to minimize the formation of undesirable by-products and to dissolve the reactants. Accordingly, at least one mole of weak acid per arylisonitrosoalkanolamine should be used. The amount of weak acid, however, may be in the range of about one (1) to about six (6) moles of acyl donor per mole of arylisonitrosoalkanolamine.

The noble metal catalyst used in the hydrogenation steps of the present invention is a noble metal catalyst such as platinum, palladium, nickel, rhodium, ruthenium, or mixtures thereof supported on an inert support such as alumina, Kiesel-Guhr support, or preferably, carbon. The most preferred hydrogenation catalyst is palladium on carbon wherein the palladium comprises from about 5 to about 25% by weight of the total weight of palladium and carbon. The amount of transition metal catalyst is in the range of about 0.1 to about 10 weight parts of catalyst (metal and support) per 100 weight pans of arylisonitrosoalkanone reactant. That amount is substantially lower than the amounts used in prior processes which produce the products of the present invention.

The reaction temperature for both hydrogenating steps shall be sufficient to maintain a desirable reaction rate. Accordingly, the temperature is in the range of about 30° to about 80° C. The completion time of both reactions depends on the amount of catalyst used and the reaction temperature. Typically, the first step is completed within a period of about one (1) to about three (3) hours.

After the first hydrogenating step, i.e. the conversion of the arylisonitrosoalkanone of Formula I to the arylalkanolamine of Formula III, is completed, sufficient amount of strong mineral acid of Formula IV is charged to the reactor to carry out the second hydrogenation step, i.e. the conversion of the arylalkanolamine to the arylalkylamine of Formula V. Examples of strong mineral acids used to carry out this step include hydrochloric acid, sulfuric acid, and phosphoric acid. The preferred acid is hydrochloric acid. Although about one (1) mole of mineral acid per mole of arylalkanolamine is sufficient to carry out the present invention, it is preferred that an excess amount in the range of about one (1) mole to about ten (10) moles of acid per mole, preferably 1–3 moles, of arylisonitrosoalkanone reactant be used in the present reaction.

The hydrogenation of arylalkanolamine to the arylalkylamine is completed within a period in the range of about one (1) to about ten (10) hours. When the reaction is completed, the products may be separated by well known techniques such as evaporation followed by recrystallization.

Any commercially available arylisonitrosoalkanone of Formula I may be used as the starting material to practice the present invention. Furthermore, the present method may be integrated with methods used to make such arylisonitrosoalkanone from other material.

II. Processes for the Preparation of an Arylalkanolamine from an Acetophenone

The following two methods are methods which integrate the above described method with two methods of preparing an arylisonitrosoalkanone of Formula I wherein $R_1$ is hydroxyl and $R_2$ is hydrogen from a corresponding acetophenone of the formula

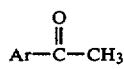

(hereinafter "Formula VI"). The arylisonitrosoalkanone is represented by the formula

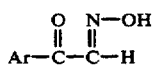

(hereinafter "Formula IA") and is sometimes hereinafter referred to as isonitrosoacetophenone.

(a) Three-Step Process for the Preparation of Substituted or Unsubstituted Isonitrosoacetophenones Followed by a Two-step Process for the Preparation of an Arylalkylamine Therefrom.

In the first method, a substituted or an unsubstituted acetophenone of Formula VI is converted to a substituted or unsubstituted isonitrosoacetophenone of Formula IA in a three-step process. The three steps are carried out in sequence in the same reactor.

In the first step, the substituted or unsubstituted acetophenone is oxidized by reacting it with a primary or a secondary alkyl alcohol of the formula $R_7$—OH (hereinafter "Formula VII") in the presence of a source of a hydrogen ion (H+) and a source of a nitrosonium ion (NO+) to form a corresponding substituted or unsubstituted phenylglyoxal acetal. The primary or secondary alcohol $R_7$—OH is typically methyl alcohol, isopropyl alcohol, sec-butyl alcohol, n-butyl alcohol or isoamyl alcohol. It is preferably present in excess of 2.0 mole equivalents, the amount required stoichiometrically for the reaction. In the case where the substituted acetophenone is 4-hydroxyacetophenone, the amount of alcohol $R_7$—OH used is from about two (2) to about ten (10) times the weight of the 4-hydroxyacetophenone or, more preferably, from about two (2) to about five (5) times the weight of the 4-hydroxyacetophenone.

The source of the hydrogen ion (H+) is a strong mineral acid, preferably hydrogen chloride or sulfuric acid. Theoretically, the acid should be present in at least a catalytic amount in the range of about 0.01 to about 0.9 moles of acid per mole of substituted acetophenone; preferably, however, it should be present in an amount of from about 0.1 to about six (6) mole equivalents of the amount of the substituted or unsubstituted acetophenone such as 4-hydroxyacetophenone, more preferably, from about one 0.4 to about three (3) mole equivalents and, most preferably, from about 0.5 to about 1.0 mole equivalents.

The source of the nitrosonium ion (NO+) can be alkyl nitrite of the formula $R_8$—O—N=O (hereinafter "Formula VII") used in combination with an acid source such as sulfuric acid, or preferably, hydrogen chloride. $R_8$ is an alkyl group having typically one (1) to ten (10) carbon atoms. This definition of $R_8$ will be applicable hereinafter, unless stated otherwise. Examples of such nitrites are methyl nitrite, ethyl nitrite, isopropyl nitrite or t-butyl nitrite. The alkyl nitrite $R_8$—O—N=O reacts with the acid to form a compound that makes the nitrosonium ion (NO+) available for the reaction and an alcohol of the formula and $R_8$—OH (hereinafter "Formula IX"). The alkyl nitrite is preferably present in an amount of from about one (1) to about five (5) mole equivalents of the amount of 4-hydroxyacetophenone, and, more preferably, from about one (1) to about three (3) mole equivalents.

When the source of nitrosonium ion (NO+) is an alkyl nitrite of Formula VIII wherein $R_8$ is a primary or a secondary radical, substituted or unsubstituted phenylglyoxal acetals of the

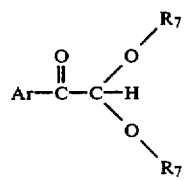

(hereinafter "Formula X")

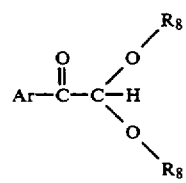

(hereinafter "Formula X"), and

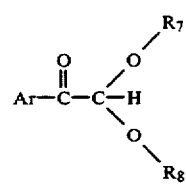

(herein "Formula XII"), are formed. These compounds are then convened, in the second step, as described below, substituted or unsubstituted phenylglyoxals of the formula $$Ar-\overset{O}{\underset{\|}{C}}-\overset{O}{\underset{\|}{C}}-H$$

(hereinafter "Formula XIII") and alcohols of Formulas VII and IX. If $R_8$ is a tertiary radical, no substituted or unsubstituted phenylglyoxal acetals of Formulas XI and XII are formed.

The oxidation reaction is carried out in the liquid phase. It presently appears that the components of the reaction mixture used to form the substituted or unsubstituted phenylglyoxal acetals of Formulas X, XI and XII may be combined in any order. The reaction mixture is preferably free of water. The reaction is exothermic and requires no heating to drive the reaction. The reaction may be cooled to a convenient working temperature. The reaction is preferably conducted at a temperature of from about $-20°$ C. to about $50°$ C., or, more preferably, from about $-10°$ C. to about $40°$ C. or, most preferably, at about $10°$ C. Depending on the reaction temperature, the conversion of the substituted or unsubstituted acetophenone to the corresponding substituted or unsubstituted phenylglyoxal acetals is completed in about one (1) hour to about four (4) hours.

The source of the nitrosonium ion ($NO^+$) can also be a nitrite salt, preferably, an alkali metal nitrite salt and, more preferably, sodium nitrite. That salt in combination with the strong mineral acid, preferably hydrochloric acid or sulfuric acid, generates in situ a compound $NO^+X_1^-$ which makes the nitrosonium ion ($NO^+$) available to the reaction.

The source of the nitrosonium ion can also be a reactant $NO^+X^-$ which is available from a source outside of the reaction, wherein $X_1$ is a halogen, an acetate, a sulfate or a phosphate. $X_1$ is preferably a halogen and, most preferably, chlorine. When the source of the nitrosonium ion is a nitrite salt or a reactant $NO^+X_1^-$ which is available from an outside source, the substituted or unsubstituted phenylglyoxal acetal formed is of the Formula X.

After the substituted or unsubstituted acetophenone is oxidized to form the corresponding substituted or unsubstituted phenylglyoxal acetal or acetals, as described above, the second step of the process of the first embodiment is carried out by hydrolyzing the substituted or unsubstituted phenylglyoxal acetal or acetals so formed in the same reactor. The hydrolysis is carried out by adding water or steam to the reaction mass. The hydrolysis step requires the presence of catalytic amounts of a strong miner at acid. In the present invention, that acid is already present in the reaction mass because it is required in the first step, i.e. the oxidation step. The products of the hydrolysis reaction are the substituted phenylglyoxals of Formula XIII and an alcohol or alcohols. In the case wherein the source of the nitrosonium ion ($NO^+$) is an alkyl nitrite of the Formula VII, the alcohol products are alcohols of the Formulas VII and IX. In the case where the source of the nitrosonium ion ($NO^+$) is a nitrite salt or a reactant $NO+X^-$ available from an outside source, the alcohol product is an alcohol of the Formula VII.

In order to bring the hydrolysis reaction to substantially full conversion, the alcohol product or products are continuously removed by vaporization as they are being generated. Accordingly, the hydrolysis reaction is carried out at temperatures which are sufficiently high to vaporize the alcohol or alcohol products. Typically, the hydrolysis reaction is carried out at a temperature in the range of from about $25°$ C. to about $100°$ C. and, preferably, from about $50°$ C. to about $100°$ C. and the water is added as hot water or steam. The hydrolysis reaction is carded out for about thirty minutes to about six hours.

The substituted or unsubstituted phenylglyoxal formed falls out of the solution and can be separated therefrom by well known techniques. Furthermore, the phenylglyoxal may remain in the reaction mass and can be used to produce further products in the same reactor, as discussed below.

Following the oxidation reaction, the phenylglyoxal of Formula XIII is reacted with hydroxylamine or a salt of hydroxylamine such as hydroxylamine hydrochloride or hydroxylamine sulfate in the presence of an acid such as hydrochloric acid or sulfuric acid. The reaction is stoichiometrically represented as follows:

$$Ar-\overset{O}{\underset{\|}{C}}-\overset{O}{\underset{\|}{C}}-H + NH_2OH \xrightarrow{H^+} Ar-\overset{O}{\underset{\|}{C}}-\overset{NOH}{\underset{\|}{C}}-H + H_2O \quad \text{(Reaction 3)}$$

The condensation reaction of glyoxal to isonitrosoacetophenone is carried out at a pH in the range of about 7 to about the pH of concentrated acid, and, preferably, below 0.5, and at a low temperature, preferably in the range of from $10°$ C. to about $65°$ C. The condensation reaction is initiated by adding 0.9 to 1.5 and, preferably, one molar equivalent of hydroxylamine, hydroxylamine hydrochloride, or hydroxylamine sulfate to the reactor containing the phenylglyoxal. The condensation reaction is completed in about five minutes to one hour, depending on the temperature and pH.

Upon the completion of the condensation reaction to form the isonitrosoacetophenone of Formula IA, any strong acid present in the reaction mass is removed therefrom. Then, the isonitrosoacetophenone is hydrogenated via Reaction 1 in the presence of a weak carboxylic acid of Formula II over a noble metal catalyst to form an arylalkanolamine of the Formula III wherein $R_2$ is hydrogen and, more particularly an arylalkanolamine of the formula:

$$Ar-\overset{OH}{\underset{|}{C}}-\overset{N-H_2}{\underset{|}{C}}-H$$
$$\phantom{Ar-C}\underset{H}{|}\phantom{C}\underset{H}{|}$$

(hereinafter "Formula IIIA"). The arylakanolamine is, then, hydrogenated via Reaction 2 by adding a strong mineral acid of Formula HX to form an arylalkylamine of the Formula IV wherein $R_2$ is hydrogen and, more particularly, an arylalkylamine of the formula:

$$Ar-\overset{H}{\underset{|}{C}}-\overset{N-H_2}{\underset{|}{C}}-H$$
$$\phantom{Ar-C}\underset{H}{|}\phantom{C}\underset{H}{|}$$

(hereinafter "Formula IVA"). In order to avoid being repetitive, reference is made to the detailed description of the hydrogenation steps above.

(b) Two-Step Process for the Preparation of Substituted or Unsubstituted Isonitrosoacetophenones In the second embodiment, a substituted or an unsubstituted acetophenone of Formula VI is convened to a substituted or unsubstituted isonitrosoacetophenone of Formula IA in a two-step process. In the first step, the acetophenone, such as 4-hydroxyacetophenone, is reacted with a source of nitrosonium ion in water in the presence of a strong mineral acid such as hydrochloric or sulfuric acid to convert it to a corresponding phenylglyoxal of Formula XIII. It should be understood that, in this embodiment, Ar, which was previously defined, should be such that the compound of Formula VI is sufficiently soluble in water to provide sufficient contact between the reactants for the reaction to proceed.

The source of a nitrosonium ion is a compound $NO^+ X_1^-$ wherein $X_1$ is a halogen, an acetate, a sulfate or a phosphate. $X_1$ is preferably a halogen and, most preferably, chlorine. The reactant $NO^+ X_1^-$ can be available from an outside source or, preferably, can be generated in situ by reacting a nitrite salt, preferably an alkali metal nitrite salt and, more preferably, sodium nitrite, with a strong acid such as hydrochloric or sulfuric acid.

In the case in which sodium nitrite is reacted with hydrochloric acid to generate a source of nitrosonium ion ($NO^+$) in situ and the source of nitrosonium ion is reacted with an acetophenone of Formula VI, such as 4-hydroxyacetophenone, the primary reactions are as follows:

(Reaction 4)

(Reaction 5)

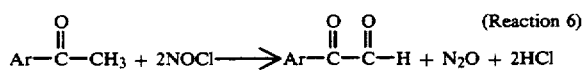

(Reaction 6)

Reaction 6 shows that two (2) mole equivalents of a nitrosonium ion ($NO^+$) are required stoichiometrically to convert one (1) mole equivalent of substituted or unsubstituted acetophenone. Therefore, at least two moles of sodium nitrite are required to generate the stoichiometric requirements of nitrosonium ion ($NO^+$) to effect maximum conversion of the substituted or unsubstituted acetophenone. Satisfactory conversions, however, are obtained with lower amounts of nitrite salt. Accordingly, the reaction is carded out by using from about one (1) to about three (3) and preferably, about 2.2 moles of sodium nitrite per mole of substituted or unsubstituted acetophenone and from about one (1) to about ten (10) and, preferably, about six (6) moles of hydrochloric acid per mole of substituted or unsubstituted acetophenone. The reaction is carried out at a temperature in the range of about 30° C. to about 90° C. and, preferably, in the range of about 40° C. to about 65° C.

In the conversion of the substituted or unsubstituted acetophenone, certain side reactions compete with Reaction 6. For example, in the case wherein 4-hydroxyacetophenone is converted, side reactions form 4-hydroxybenzoyl formic acid and 4-hydroxybenzoic acid. In order to minimize the side reactions and the loss of NOCl, it is preferred that the sodium nitrite in an aqueous solution be added gradually to an aqueous solution of substituted or unsubstituted acetophenone and hydrochloric acid over a period of about 0.5 to about ten (10) hours and, more preferably, over a period of about one (1) to about four (4) hours.

In the second step of this embodiment, the substituted phenylglyoxal of Formula XIII produced in the first step is reacted with hydroxylamine or a salt thereof in the presence of an acid such as hydrochloric acid or sulfuric acid to form a substituted isonitrosoacetophenone of Formula IA. The reaction is represented by Reaction 3.

The first and second steps are preferably carried out in the same reactor. The condensation reaction is initiated by adding one molar equivalent of hydroxylamine and the acid to the reactor containing the reaction mass of the first step. The reaction is carried out at a low pH, from about 7 to about the pH of concentrated acid, and preferably, below 0.5, and at a low temperature, preferably, in the range of from about 10° C. to about 65° C. The reaction is completed in about five (5) minutes.

Upon the completion of the reaction, the strong acid is removed and the isonitrosoacetophenone of Formula IA is subjected to the hydrogenation reactions depicted by Reactions 1 and 2, as previously described, to form, first, an arylalkanolamine of Formula IIIA and then, an arylalkylamine of Formula IV A.

The following examples further illustrate the invention but are not to be construed as limitations of the invention contemplated herein.

EXAMPLE 1

Preparation of p-Hydroxyisonitrosoacetophenone.

Methyl nitrite (0.0808 moles) was added to a solution containing 50 grams (0.3672 moles) of 4-hydroxyacetophenone in 200 milliliters of methanol and 8 grams of hydrochloric acid (HCl). The reactor was stirred during the reaction and for a short time following addition of the methylnitrite.

Following completion of the oxidation the reactor was allowed to warm to about 30° C. Steam was sprayed into the reactor causing the methanol to distill off.

After removal of the methanol by distillation, another 400 milliliters of water were added to the reactor. The solution was allowed to cool to 60° C. and 48.03 grams of concentrated HCl were added. After the addition of the HCl a solution of 25.77 grams (0.3708 moles) of $NH_2OH \cdot HCl$ in 40 milliliters of water was added over a five (5) minute period.

Following addition of the $NH_2OH \cdot HCl$ the reactor was cooled in an ice bath. The solids were filtered off and dried under a vacuum. Weighing the samples showed a yield of eighty (80) percent based on the starting acetophenone.

EXAMPLE 2

Preparation of p-Hydroxyisonitrosoacetophenone.

A solution of 27.2 grams (0.44 moles) of $NaNO_2$ in 100 milliliters of water was added over a period of three (3) hours to a stirred solution of 27.2 grams (0.2 moles) 4-HAP in 74.6 milliliters of concentrated HCl and 93 milliliters of water at 55° C.

Following the addition of the $NaNO_2$, 49.24 grams (0.3 moles) of $(NH_2OH)_2 \cdot H_2SO_4$ was added. The $(NH_2OH)_2 \cdot H_2SO_4$ was added slowly at first to quench any NO-X, and then added all at once, whereupon HINAP precipitated in a yield of about 70 percent, based on the 4-HAP starting material.

EXAMPLE 3

Preparation of p-Hydroxyphenylethanol Amine Acetate (Octopamine HOAc).

Two grams of a 10% palladium on carbon catalyst (50% H$_2$O wt./wt.) was added to a one (1) liter zipperclave along with 200 grams of acetic acid or water. The reactor was then sealed and degassed with nitrogen then hydrogen. Under 70 psig of hydrogen the catalyst was stirred and heated to 30° C. The reactor was then degassed with nitrogen and opened. 4-Hydroxy-α-isonitrosoacetophenone (100 g, 0.6061 mol.) and HOAc (150 g) was then added to the reactor. The zipperclave was sealed and degassed with nitrogen then hydrogen. Under 70 psig of hydrogen and at 30° C., the stirring was initiated. The reaction heated itself rapidly while consuming the first two (2) equivalents of hydrogen. The temperature was kept below 50° C. for this portion of the reaction. The reaction was then heated to 60° C. and was allowed to consume the third equivalent of hydrogen. The reaction solution was degassed with nitrogen then analyzed. It contained 115.6 gm, 90% yield of Octopamine HOAc.

EXAMPLE 4

Preparation of p-Hydroxyphenylethyl-Amine Hydrochloride (Tyramine HCl).

Two grams of a 10% palladium on carbon catalyst (50% H$_2$ wt./wt.) was added to a one (1) liter zipperclave along with 200 grams of acetic acid or water. The reactor was then sealed and degassed with nitrogen then hydrogen. Under 70 psig of hydrogen the catalyst was stirred and heated to 30° C. The reactor was then degassed with nitrogen and opened. 4-Hydroxy-α-isonitrosoacetophenone (100 g, 0.6061 mol.) and HOAc (150 g was then added to the reactor. The zipperclave was sealed and degassed with nitrogen then hydrogen. Under 70 psig of hydrogen and at 30° C., the stirring was initiated. The reaction heated itself rapidly while consuming the first two (2) equivalents of hydrogen. The temperature was kept below 50° C. for this portion of the reaction. The reaction was then heated to 60° C. and was allowed to consume the third equivalent of hydrogen. A solution of 37% (wt./wt.) HCl was then added to the reaction. After the addition of HCl the last equivalent of hydrogen was consumed and the reaction was degassed with nitrogen and opened. The reaction was filtered to remove the catalyst then concentrated by evaporating the solvent. Upon cooling the tyramine HCl (84.2 gm, 80% yield) precipitated out as a white solid.

While the invention is described with respect to specific embodiments, modifications thereof can be made by one skilled in the art without departing from the spirit of the invention. The details of said embodiments are not to be construed a limitation except to the extent indicated in the following claims.

What is claimed is:

1. A method of preparing a substituted or an unsubstituted arylalkylamine from a corresponding substituted or unsubstituted arylisonitrosoalkanone, comprising the steps of:
    first converting the arylisonitrosoalkanone to a corresponding arylalkanolamine; and
    second converting the arylalkanolamine wherein the first converting step includes the step of reacting the arylisonitrosoalkanone with hydrogen in the presence of a week carboxylic acid and a noble metal catalyst, and wherein the second converting step includes the step of reacting the arylalkanolamine with hydrogen in the presence of a strong acid and transition metal catalyst to the arylalkylamine.

2. The method according to claim 1 wherein the first converting step is carried out in the absence of a strong acid.

3. The method according to claim 1 wherein the arylalkylamine is of the formula

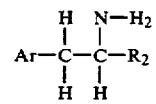

and the arylisonitrosoalkanone is of the formula

wherein Ar is an unsubstituted phenyl or naphthyl radical or a substituted phenyl or naphthyl radical substituted independently at one or more of the substitutable positions, R$_1$ is a hydroxyl, an alkyloxy or a benzyl radical, and R$_2$ is hydrogen or a C$_1$–C$_8$ alkyl or cycloalkyl radical.

4. The method according to claim 3 wherein the substituted phenyl radical or the substituted naphthyl radical is substituted with substituents which are independently a hydroxyl radical, an alkoxy radical, an acyloxy radical, a substituted or unsubstituted branched or unbranched alkyl radical R$_4$ containing one (1) to five (5) carbon atoms, a substituted or an unsubstituted phenyl radical R$_5$ or a substituted or an unsubstituted benzyl radical R$_6$.

5. The method according to claim 4 wherein the substituted alkyl radical R$_4$ is independently substituted in one or more positions with a halogen, a hydroxyl, a sulfonic acid or a sulfinic acid radical; and the substituted phenyl radical R$_5$ and the substituted radical R$_6$ are independently substituted in one or more positions with radicals selected independently from the group of a hydroxyl radical, sulfonic acid radical, sulfinic acid radical, alkyl radicals having one (1) to five (5) carbon atoms and alkoxy radicals having one (1) to five (5) carbon atoms.

6. A method of preparing a substituted or an unsubstituted arylalkylamine of

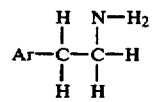

comprising the step of hydrogenating an arylalkanolamine of the formula

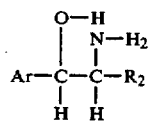

in the presence of a strong acid and a transition metal catalyst wherein Ar is an unsubstituted phenyl or naphthyl radical or a substituted phenyl or naphthyl radical substituted independently at one or more of the substitutable positions, R$_1$ is a hydroxyl, an alkyloxy or a benzyl radical, and R$_2$ is hydrogen or a C$_1$–C$_8$ alkyl or cycloalkyl radical.

* * * * *